United States Patent [19] [11] Patent Number: 5,008,409
Narisada et al. [45] Date of Patent: Apr. 16, 1991

[54] PROCESS FOR PREPARING 1,4-BRIDGED CYCLOHEXANE CARBOXYLIC ACID DERIVATIVES

[75] Inventors: Masayuki Narisada, Ibaraki; Mitsuaki Ohtani, Nara; Fumihiko Watanabe, Kitakatsuengi; Kyozo Kawata, Hirakata, all of Japan

[73] Assignee: Shionogi & Co., Ltd., Osaka, Japan

[21] Appl. No.: 447,513

[22] Filed: Dec. 7, 1989

[30] Foreign Application Priority Data

Dec. 14, 1988 [JP] Japan ................................. 63-315970

[51] Int. Cl.$^5$ ................. C07D 307/00; C07C 311/16; C07C 311/20
[52] U.S. Cl. .................................... 549/463; 562/407
[58] Field of Search ......................... 549/463; 562/427

[56] References Cited
FOREIGN PATENT DOCUMENTS
0226346 6/1987 European Pat. Off. .
0312906 4/1989 European Pat. Off. .

OTHER PUBLICATIONS
Narisada et al., J. Med. Chem. 1988, 31, 1847–1854.

Primary Examiner—Bernard I. Dentz

[57] ABSTRACT
A process for preparing a compound of Formula (I):

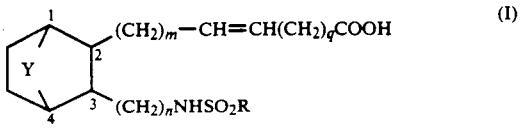

wherein R is phenyl or phenyl substituted with hydroxy, lower alkoxy, halogen or lower alkyl; Y is unsubstituted or substituted methylene, ethylene, vinylene or oxygen; m is 0 or 1; n is 0, 1 or 2; and q is 1, 2, 3 or 4; with the limitation that when m is 0, n is not 0, and when m is 1, n is not 2, which process comprises:
(a) reacting an aldehyde of Formula (II);

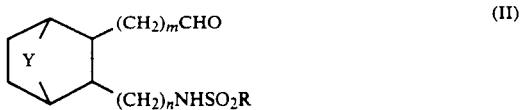

wherein R, Y, m and n are as defined above, under reaction conditions for the Wittig Reaction with a ylide of Formula (III):

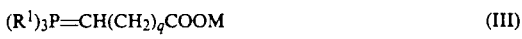

wherein $R^1$ is $C_1$–$C_8$ alkyl or aryl, M is an alkali metal and q is as defined above;
(b) treating the reaction mixture of step (a) with an alkaline earth metal halide under alkaline conditions to form the alkaline earth metal salt of the carboxylic acid of Formula (I);
(c) extracting the alkaline earth metal salt of the carboxylic acid of Formula (I) in an organic solvent; and
(d) recovering the free carboxylic acid of Formula (I) from the organic solvent.

5 Claims, No Drawings

PROCESS FOR PREPARING 1,4-BRIDGED CYCLOHEXANE CARBOXYLIC ACID DERIVATIVES

This invention relates to a process for preparing 1,4-bridged cyclohexane carboxylic acid derivatives which are clinically useful as an antagonist against thromboxanes, particularly, thromboxane $A_2$ ($TXA_2$) More specifically, it relates to a process suited for industrial mass-production of a 1,4-bridged cyclohexane carboxylic acid derivative of Formula (I):

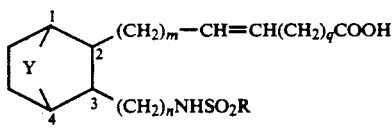

(I)

wherein R is naphthyl, phenyl or phenyl substituted with hydroxy, lower alkoxy, halogen or lower alkyl; Y is unsubstituted or substituted methylene, ethylene, vinylene or oxygen; m is 0 or 1; n is 0, 1, or 2; and q is 1, 2, 3 or 4; with proviso that when m is 0, n is not 0, and when m is 1, n is not 2.

Thromboxanes are known to be biologically active substances and synthesized enzymatically from eicosapolyenoic acids, such as arachidonic acids found in various animal tissues, for example, platelets, vascular walls, and the like. Among thromboxanes, thromboxane $A_2$ ($TXA_2$) has been proved to exhibit many significant biological activities, such as aggultination of platelets and contraction of smooth muscle of various organs, e.g., bronchus, coronary artery, pulmonary artery, and the like, at a relatively low serum level of about $10^{-11}$-$10^{-12}$M. Because of these biological activities, $TXA_2$ has been considered to be one of the major causes of myocardial infarction, cerebral infarction, bronchial asthma and thrombosis. Therefore, $TXA_2$ synthetase inhibitors which inhibit an enzyme responsible for the biosynthesis of $TXA_2$, or $TXA_2$ receptor antagonists which antagonize the binding of $TXA_2$ to its receptor, have been expected to be practically useful in the treatment and prevention of the above-mentioned diseases. However, the inhibitors are not suited for clinical use because inhibition of $TXA_2$ synthesis may result in accumulation of the precursor, i.e., prostaglandin $H_2$, which is believed to exhibit a biological activity similar to that of $TXA_2$. To the contrary, the receptor antagonists are thought to be useful for treating and preventing $TXA_2$-dependent diseases because they are not affected by the accumulated prostaglandin $H_2$.

In view of the above, the present inventors made extensive study and found that 1,4-bridged cyclohexane carboxylic acid derivatives, which are analogous to $TXA_2$ or prostaglandin $H_2$, serve as an antagonist against $TXA_2$ and are chemically and biochemically stable [see, Japanese Patent Publication (Kokai) No. 139161/1988].

According to the above-mentioned Japanese Patent Publication, a typical compound of Formula (I) in which R is phenyl, Y is methylene, m is 1, n is 0, and q is 3, is prepared in the manner as described below starting from the compound of Formula 1:

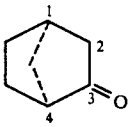

1

Specifically, the amine of Formula 2:

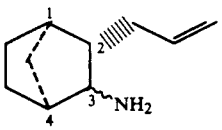

2 is first prepared from the above ketone 1 by introducing an allyl group at the 2-position, converting the carbonyl group at the 3-position into oxime, and reducing the oxime to an amino group. After protection of the amino group, the allyl group of said amine 2 is oxidized to give an epoxide, which is then oxidatively cleaved to give an aldehyde of Formula 3:

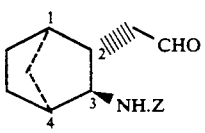

3 wherein Z is an amino-protecting group. The aldehyde 3 is then reacted with the ylide of Formula:

according to the teaching of Wittig et al. [Wittig Reaction, G. Wittig and U. schöllkopf, Ber. 87, 1318 (1954); G. Wittig and W. Hagg, Ibid. 88, 1964 (1955)] and subsequently esterified to give an ester of Formula 4:

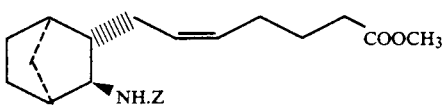

4

The reaction mixture is chromatographed on silica-gel to separate the desired amino-protected ester 4 from acidic contaminants or their esters which result from the excess of the reagents employed. The amino-protected ester is then deprotected and the resulting amine is sulfonated with a sulfonyl halide, such as phenylsulfonyl chloride, to obtain a desired compound of Formula (I).

It will be easily understood that the above procedure is too complicated to apply to an industrial mass-production of the compound (I). Especially, the chromatographic purification of protected ester 4 is very time-consuming and requires a large amount of solvents.

In view of the above, the inventors have continued the study in order to establish an alternative synthetic process more suited for mass production of these compounds, especially the compounds having the Formula (I), and succeeded in the development of a useful method for industrial mass-production of said compounds.

Thus, the present invention provides for an industrially applicable process for the preparation of 1,4- bridged cyclohexane carboxylic acid derivative of Formula (I), which comprises:

(a) reacting an aldehyde of Formula (II):

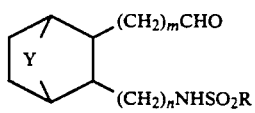
(II)

wherein R, Y, m and n are as defined above, under reaction conditions for the Wittig Reaction with a ylide of Formula (III):

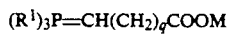
(III)

$R^1$ is $C_1$-$C_8$ alkyl or aryl, M is an alkali metal and q is as defined above;

(b) treating the reaction mixture of step (a) with an alkaline earth metal halide under alkaline conditions so that the resulting carboxylic acid of Formula (I) may form an alkaline earth metal salt;

(c) extracting the alkaline earth metal salt of the carboxylic acid of Formula (I) in an organic solvent; and (d) recovering the free carboxylic acid of Formula (I) by acidifying the organic solvent to dissolve the salt.

The above-mentioned procedure of the invention has been established through finding of the difference of the solubilities of alkaline earth metal salts of desired compound (I) and undesired acidic contaminants in organic solvents. That is, the compound (I) is fairly insoluble in organic solvents in the form of an alkali metal salt but soluble in the form of an alkaline earth metal salt. To the contrary, acidic by-products of ylide (III) remain slightly soluble or insoluble in organic solvents, even after the replacement of an alkali metal by an alkaline earth metal.

In the above process, it is preferred to partition the reaction mixture obtained in step (a) between water and toluene, and to discard the toluene layer containing neutral by-products, and to employ the aqueous layer containing the aimed product as an alkali salt in the next step (b) described above.

For the purpose of the present invention, as disclosed and claimed herein, the following terms are defined as below.

The term "lower alkyl" refers to a straight or branched saturated hydrocarbon radical having one to eight carbon atoms, including methyl, ethyl, n-propyl, isopropyl, butyl, isobutyl, sec-butyl, tert-butyl, pentyl, isopentyl, neopentyl, 1-methylbutyl, 1,2-dimetylbutyl, hexyl, heptyl, octyl, and the like.

The term "lower alkoxy" refers to $C_1$-$C_8$ alkoxy, including methoxy, ethoxy, propoxy, isopropoxy, butoxy, pentoxy, hexyloxy, heptyloxy, octyloxy, or the like.

The term "substituted methylene" refers to ethylidene, dimethylmethylene, methylethyl-methylene, diethylmethylene, and the like.

The term "halogen" refers to chlorine, bromine, iodine and fluorine.

The term "alkali metal" refers to lithium, potassium or sodium.

The term "alkaline earth metal" refers to calcium, barium or magnesium.

The term "ester of acetic acid" refers to methyl acetate, ethyl acetate or butyl acetate.

The term "aryl" refers to phenyl or naphtyl.

The preferred example of R is phenyl, o-tolyl, m-tolyl, p-tolyl, 4-ethylphenyl, 4-pentylphenyl, 4-hydroxyphenyl, 4-methoxyphenyl, 4-fluorophenyl, 4-bromophenyl, or 4-chlorophenyl. The preferred example of Y is methylene, dimethylmethylene, ethylene, vinylene or oxygen.

Particularly preferred carboxylic acid derivatives of Formula (I) are the compounds (I) wherein R is phenyl, p-tolyl, 4-hydroxyphenyl or 4-bromophenyl; Y is methylene or oxygen; and m is 1, n is 0 and q is 3; or m is 0, n is 1 and q is 3.

Preferred alkaline earth metals are magnesium, calcium, and barium, with calcium being most preferred. Preferable organic solvent is ethyl acetate.

The aldehyde (II), the starting material of the process of the present invention, can be prepared using any processes known in the art. However, it is convenient to prepare the aldehyde in accordance with the procedure described in the afore-mentioned Japanese Patent Publication (Kokai) No. 139161/1988. Alternatively, it can be prepared by sulfonating above-mentioned amine 2 and ozonolysis of resulting allyl sulfonamide.

The preparation of another starting material, ylide (III), is well known to those skilled in the art. For instance, the ylides are readily obtained by reacting phosphines, such as trialkyl- or triaryl-phosphines, e.g., triphenyl-, trimethyl- or triethylphosphine, with halogeno alkanoic acids having an alkyl group to be condenced, e.g., 4-bromobutyric acid, 5-bromovaleric acid, or 3-bromopropionic acid. The preferred phosphoranes are alkali metal salts of carboxyalkylenetrialkyl- or carboxyalkylenetriaryl-phosphoranes, most preferably, potassium carboxyalkylenephosphorane. The reaction can be carried out in an inert solvent such as ether, tetrahydrofuran, n-hexane or dimethylsulfoxide, most preferably tetrahydrofuran, at a temperature in the range of $-50°$-$40°$ C. for 1-12 hours. The base employed in this reaction can be selected from the group of potassium t-butoxide, dimsyl sodium, dimsyl potassium, sodium hydride, butyl lithium, potassium t-butoxide, lithium di-isopropylamide, and the like.

According to the present invention, the aldehyde (II) is reacted under reaction conditions for the Wittig Reaction using a large excess amounts of ylide (III). Reaction conditions for the Wittig Reaction of said ylide (III) with the above-mentioned aldehyde (II) is well known to these skilled in the art. When the Wittig Reaction is over, the reaction mixture contains alkali metal salts (I') of carboxylic acid (I), alkali metal salts (III') of acidic by-products of ylide (III), and neutral by-products. Among them, only neutral by-products are soluble in organic solvents, such as toluene, and can be removed by extraction. The conversion of salt (I') to corresponding alkaline earth metal salt (I'') can be conducted under alkaline conditions, in the pH range of 8 to 9. After replacement of an alkali metal with an alkaline earth metal, the separation of desired salt (I'') from contaminants is conducted by extraction with organic solvents and recovery of free carboxylic acid (I) from said salt (I'') is conducted in the usual manner.

In the preferred embodiment of the process of the invention, the reaction mixture in step (a) is partitioned between toluene and water, and the aqueous layer is separated and made alkaline followed by treatment with an alkaline earth metal halide under alkaline conditions, as previously mentioned. The resulting mixture is partitioned between ethyl acetate and water. The organic layer is taken and made acidic, and condensed to dryness. The residue is purified in the usual manner, for example by recrystallization, whereby the desired free acid (I) is obtained in high purity.

Thus, the essence of the recovery system of the desired product (I) from the reaction mixture of the Wittig Reaction can be summarized in the following manner:

(1) removing the neutral by-products from the alkali salts of carboxylic acids by extraction with an organic solvent,
(2) converting the remaining alkali salts of carboxylic acid (I) and acidic by-products of ylide (III) in an aqueous phase into corresponding alkaline earth metal salts under alkaline conditions,
(3) extracting the mixture of step (2) with an organic solvent in which the alkaline earth metal salts of carboxylic acid (I) are capable of dissolving and
(4) recovering and purifying the free carboxylic acid (I) from the organic extract of step (3).

For the purpose of the invention, it is not essential to conduct the above steps in this order. For example, step (1) may be conducted after step (2), which is followed by steps (3) and (4). It is also notable that the present process is effective to obtain any form of final product (I), such as optically active isomer or racemic mixture, using appropriate starting compound (II).

According to the present invention, the desired carboxylic acid (I) can be readily prepared using the aldehyde of Formula (II) as a starting compound without employing chromatographic procedure.

The following examples further illustrate the processes of the invention. It will be understood that the example is illustrative and in no way meant to be construed as limiting the scope of the invention.

EXAMPLE 1

5(Z)-7-[2-Exo-3-endo-3-phenylsulfonylaminobicyclo[2,2,1]hept-2-yl]-5-heptenoic acid A. Wittig Reaction

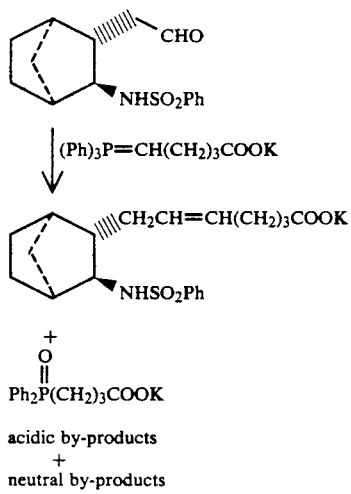

acidic by-products
+
neutral by-products

A suspension of 18 g of 4-carboxybutyl triphenylphosphoniumbromide (1.5×27.45 mmol) in 85 ml of tetrahydrofuran is stirred at −10° C. for 1 hour and allowed to cool. To the mixture was added 9 g (3×27.45 mmol) of potassium t-butoxide at 0° C. over 20 minutes and stirred at −10° C. for 1 hour. A solution of 8 g (27.45 mmol) of formylamide (IIa) in 29 ml of tetrahydrofuran is divided into three portions of 19 ml, 7 ml and 3 ml, and the 19 ml portion is added to the above mixture over 30 minutes. After stirring the mixture at −10° C. for 20 minutes, 1.5 g (0.5×27.45 mmol) of potassium t-butoxide is added while the reaction mixture being stirred at the same temperature for 20 minutes. To the mixture is added the 7 ml portion of formylamide (IIa) solution over 20 minutes, and then the reaction mixture being stirred at −10° C. for 20 minutes. After the addition of 0.62 g (0.2×27.45 mmol) of potassium t-butoxide, the mixture is stirred at the same temperature for 20 minutes. To the mixture is then added the 3 ml portion of formylamide solution over 10 minutes and stirred at 0° C. for 1 hour. The resulting reaction mixture can be used as such in the next step.

B. Separation

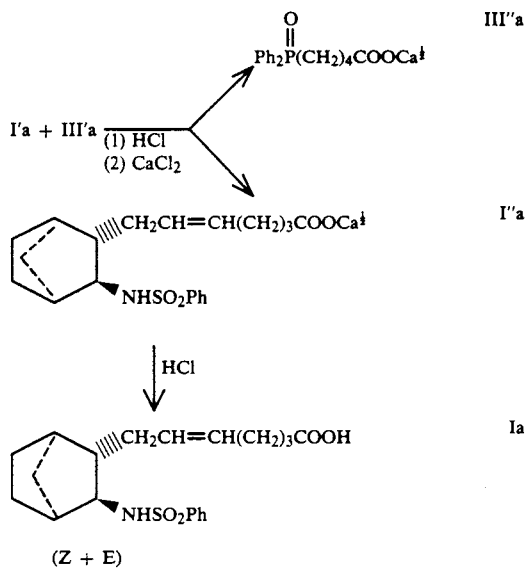

The reaction mixture obtained in the same manner as described in the above A using 6.8 g of starting compound (IIa) is poured into a mixture of water/toluene (200 ml/100 ml, adjusted to 5° C.) and the aqueous layer containing the salts (I'a) and (III'a) are separated. To the aqueous solution is dropwise added 18% HCl so as to adjust the pH to 8.0, and a mixture of ethyl acetate and 20 ml of an aqueous 40% calcium chloride solution (4 equivalents) is added thereto. The mixture is stirred for 20 minutes at 20° C. and separated. The aqueous layer is extracted with ethyl acetate, and the each organic extract is washed with water (3×) and the washings containing the salt (III″a) are discarded. The ethyl acetate solutions containing the salt (I″) are combined and water is added thereto. After cooling to 5° C., the aqueous layer is adjusted to pH 1.5 with 4.4 ml of 18% HCl, stirred for 5 minutes, and separated. The aqueous layer is extracted with ethyl acetate, and each extract is washed with 20% saline (2×). The ethyl acetate extracts are combined and decolorized by shaking with silica-gel for 10 minutes. The silica-gel is removed by filtration and the ethyl acetate solution is condensed to dryness under reduced pressure at 40° C. to obtain 10 g of an oily residue, which is then dissolved in ethanol, and water is added thereto. The mixture is seeded with crystals of the compound (Ia) and stirred for 4 hours at 7° C. The precipitates are collected by filtration and washed with 30% ethanol. The wet cristalline product is air-dried at 40° C. for 7 hours to afford 7.2 g of crude product (Ia) (yield, 70%, based on the compound (IIa)). Physical properties of the intermediate calcium salt (I"a) and the desired compound (Ia) are shown below.

Elementary analysis (for $C_{40}H_{52}N_2O_8S_2Ca \cdot 1.3H_2O$); Calcd.: C;58.84, H;6.74, N;3.43, Ca;4.91; Found: C;58.66, H;6.76, N;3.42, Ca;4.72.

HPLC analysis of the product:

Crude (Ia): Z form, 90%; E form, 7%.

Free carboxylic acid (IIIa); 1%.

The above crude product (Ia) is recrystallized from toluene to give a purified product (Ia) which contains more than 99.5% of Z form according to HPLC analysis. Physical properties of the purified compound (Ia) are shown below.

M.p.=89.9°–90.9° C.,

IR$\nu$max (KBr): 3275, 3255, 1713, 1319, 1162.

Elementary analysis (for $C_{20}H_{27}NO_4S$); Calcd. C;63.63, H;7.21, N;3.71, S;8.49, Found : C;63.78, H;7.30, N;3.68, S;8.45 .

The processes of above B and C were repeated using barium or magnesium instead of calcium. The results are shown in the following table.

TABLE I

| salt | partition | HPLC yield Z + E(%) | III"a |
|------|-----------|---------------------|-------|
| BaCl$_2$ | ethyl acetate | 88.6 | 0.5 |
|  | water | 13.4 | 34.5 |
| MgCl$_2$ | ethyl acetate | 69.5 | 1.3 |
|  | water | 15.2 | 41.5 |

Table I shows that the solubility of alkaline earth metal salts of desired compound (I) in ethyl acetate is significantly higher than the salts of ylide-derived product, which demonstrates the usefulness of the present method in mass production of carboxylic acids (I).

What we claim is:

1. A process for preparing a compound of Formula (I):

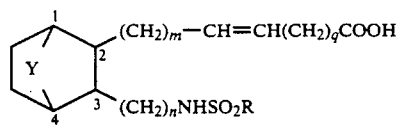

wherein R is phenyl or phenyl substituted with hydroxy, lower alkoxy, halogen or lower alkyl; Y is unsubstituted or substituted methylene, ethylene, vinylene or oxygen; m is 0 or 1; n is 0, 1 or 2; and q is 1, 2, 3 or 4; with proviso that when m is 0, n is not 0, and when m is 1, n is not 2, which process comprises:

(a) reacting an aldehyde of Formula (II);

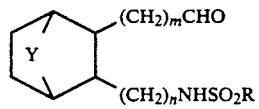

wherein R, Y, m and n are as defined above, under reaction conditions for the Wittig Reaction with a ylide of Formula (III):

wherein R$^1$ is C$_1$–C$_8$ alkyl or aryl, M is an alkali metal and q is as defined above;

(b) treating the reaction mixture of step (a) with an alkaline earth metal halide under alkaline conditions to form the alkaline earth metal salt of the carboxylic acid of Formula (I);

(c) extracting the alkaline earth metal salt of the carboxylic acid of Formula (I) in an organic solvent; and (d) recovering the free carboxylic acid of Formula (I) from the organic solvent.

2. The process of claim 1 wherein the reaction mixture of step (a) is extracted with water and the aqueous extract is used in step (b) in place of the reaction 3. The process of claim 1 wherein the alkaline earth metal halide is magnesium, calcium or barium halide.

4. The process of claim 1 wherein the organic solvent is ethyl acetate.

5. The process of claim 1, wherein the alkaline earth metal halide is calcium halide and the organic solvent is ethyl acetate.

* * * * *